United States Patent [19]
Santerre

[11] Patent Number: 6,127,507
[45] Date of Patent: Oct. 3, 2000

[54] FLUOROLIGOMER SURFACE MODIFIERS FOR POLYMERS AND ARTICLES MADE THEREFROM

[76] Inventor: Paul J. Santerre, 124 Edward St., Toronto, Canada, M5G 1G8

[21] Appl. No.: 09/198,268

[22] Filed: Nov. 24, 1998

Related U.S. Application Data

[63] Continuation of application No. 08/690,108, Jul. 31, 1996
[60] Provisional application No. 60/001,883, Aug. 3, 1995.

[51] Int. Cl.[7] .................................................. C08G 18/10
[52] U.S. Cl. ............................... 528/66; 528/65; 528/44; 428/423.1; 525/88; 525/92 C; 525/92 B; 525/92 E; 525/92 F; 525/93; 525/92 T; 525/92 R; 525/92 A; 525/130; 525/127; 525/129; 525/453; 525/454; 525/455; 525/457; 525/458
[58] Field of Search .................................. 528/65, 66, 44; 428/423.1; 525/88, 93, 92 C, 92 B, 92 E, 92 F, 92 T, 92 R, 92 A, 130, 127, 129, 453, 454, 455, 457, 458

[56] References Cited

U.S. PATENT DOCUMENTS

| | | | |
|---|---|---|---|
| 3,872,058 | 3/1975 | Gresham | 528/70 |
| 5,543,200 | 8/1996 | Hargis et al. | 428/122 |
| 5,589,563 | 12/1996 | Ward et al. | 528/44 |

FOREIGN PATENT DOCUMENTS

| | | |
|---|---|---|
| 0 231 927 | 8/1987 | European Pat. Off. . |
| WO 95/26993 | 10/1995 | WIPO . |

*Primary Examiner*—Margaret G. Moore
*Attorney, Agent, or Firm*—Pillsbury Madison & Sutro LLP

[57] ABSTRACT

A composition comprising in admixture with a polymer, preferably a polyurethane, and a compatible surface-modifying macromolecule having (i) a central portion of a segmented block oligomeric copolymer comprising at least one polar hard segment, and (ii) -ω terminal polyfluoro oligomeric groups, in a surface modifying enhancing amount. The composition is of use in providing articles having improved surface properties, particularly, medical devices having improved resistance to enzyme degradation with acceptable blood compatibility.

18 Claims, No Drawings

FLUOROLIGOMER SURFACE MODIFIERS FOR POLYMERS AND ARTICLES MADE THEREFROM

This is a continuation application of U.S. application Ser. No. 08/690,108 filed Jul. 31, 1996 which was based on provisional U.S. application No. 60/001,883 filed Aug. 3, 1995 and claims priority benefit based on said earlier filed applications.

FIELD OF THE INVENTION

This invention relates to fluoroligomers; compositions comprising said fluoroligomers as surface-modifiers in admixture with polymers, particularly, polyurethanes; articles made from said admixture, particularly medical devices; and methods of preparation of said fluoroligomers.

BACKGROUND TO THE INVENTION

Segmented polyurethanes are used in the manufacture of many conventional blood-contacting medical devices, such as pacemaker leads and connectors, vascular grafts, self-sealing arteriovenous access grafts and diagnostic catheters (1–3). The chemical structure of such polyurethane elastomers provides high tensile strength, lubricity, good abrasion resistance, ease of handling, such as extruding and bonding, and good "biocompatibility" (3,4). Although the devices provide useful short-term utility, their long-term function still remains a problem (5). One deficiency of these devices is due to the foreign nature of the implant materials with respect to the body and leads to the eventual degradation of the material (6). The consequences of the material degradation of the device inside the body includes the loss of materials' tensile strength and surface cracking (7,8). It has been found that hydrolysis and oxidation of polyurethanes in vivo were both possible causes of the degradation (8,9). In addition to the degradation of the polyurethanes, thrombus formation on the surface of polyurethane materials also presents a problem. Attempts to overcome the thrombus problem include the incorporation of heparin (10), albumin (11) and endothelial cells (12). The permanent binding of biologically active moieties to polymer chains or polymer surfaces has also been studied (13, 14). However, the main drawback of these biologically modified materials is that they suffer from the lower reproducibility of the surface modification and the effective lifetime of the components. Thus, although some new polymers have been developed with improved stability (7), no satisfactory alteration of polyurethanes has been attained.

The addition of polymeric surface additives into base polyurethanes in order to change the surface chemistry while the bulk properties are kept intact has been studied (15).

U.S. Pat. No. 4,861,830—Ward et al, issued Aug. 29, 1989, describes polymer admixtures formed from a base polymer and thermoplastic copolymer additives having polar hard segments and polar and non-polar soft blocks in graft or block copolymer form, for use in biomedical devices. U.S. Pat. No. 5,235,003—Ward et al, issued Aug. 10, 1993, describes novel linear polysiloxane-polyacetone block copolymers, particularly polysiloxane-polycaprolactone linear blocked copolymers, miscible with nylon for use as surface-modified nylon articles. U.S. Pat. No. 4,935,480—Zdrahala et al, issued Jun. 19, 1990, describes non-blocking hemocompatible, thermoplastic, fluorinated polyetherurethanes made from polyether glycols, isocyanates, chain extenders and non-fluorinated polyols. The method of preparation includes two steps in which the fluorinated glycol is reacted initially with the diisocyanate to give a prepolymer having terminal isocyanate groups. The prepolymer is subsequently reacted with the chain extender and non-fluorinated polyol. The fluorinated polyetherurethane has use in medical devices.

Ward et al (16) describes the presence of surface-active oligomeric terminal groups in linear base polymer polyurethaneureas as new biomaterials. Y. -W. Tang et al (17) describes a series of fluorine-containing polyurethane surface-modifying macromolecules having improved bioresistance and biocompatibility.

Fluorinated polymers are generally hydrolytically stable materials and have been used as coating materials (18). In addition, fluorinated polymers have exhibited good blood compatibility characteristics. The graft of a perfluorodecanoic acid to a polyurethane has been shown to enhance blood compatibility (19). This study focused on the use of modifying techniques for polyurethanes that contain fluoropolymeric segments. The macromolecular additives were introduced into the base polyurethane with the purpose of altering the surface chemistry without compromising the bulk properties of the base polyurethane.

However, there is, still, a need for materials for use in the manufacture of articles having acceptable surface properties, particularly, medical device implants requiring improved mechanical properties, blood compatibility and long term biostability.

PUBLICATIONS

The following references are referred to herein.
1. Pourdeyhimi, B.; Wagner, D., J. Biomed. Mater. Res. 1986, 20, 375
2. Hayashi, K., Biomaterials, 1986, 6, 82
3. Lelah, M. D.; Cooper, S. L., "Polyurethanes in Medicine", CRC Press: Boca Raton, Fla., 1986.
4. Coleman D. L.; Meuxelaar, H. L. C.; Kessler, T. R.; Mclennan, W. H.; Richards, J. M.; Gregonis, D. E., J. Biomed. Mater. Res. 1986, 20, 417
5. Stokes, K.; Cobian, D., Biomaterials, 1982, 3, 225
6. Szycher; M., J. Biomat. Appl., 1988, 3(2), 383
7. Coury, A. J.; Slaikeu, P. C.; Cahalan, P. T.; Stokes, K. B., Hobot, C. M., J. Appl. 1988, 3(2), 130–179
8. Parins, D. J.; Black, K. M.; Mccoy, K. D., Horvath, N., "In Vivo Degradation of a Polyurethane", St. Paul, Minn., Cardiac Pacemakers, Inc., CPI4-511-281, 1981
9. Stokes, K.; Urbanski, P.; Upton, J., J. Biomater Sci. Polymer Ed., 1990, 1(3), 207
10. Shibuta, R.; Tanaka, M.; Sisido, M.; Imanishi, Y., J. Biomed. Mater. Res., 1986, 20 971
11. Neumann, A. W.; Moscarello, M. A.; Zingg, W.; Hum, O. S.; Chang.; S. K., J. Polym. Sci., Polym. Symp., 1979, 66, 391
12. Herring, M.; Baughman, S.; Kesler, K., Surgery, 1984, 96, 745
13. Ueda, T.; Watanabe, A.; Ishihara, K.; Nakabayashi, N., J. Biomater. Sci. Polymer Edn., 1991, 3(2), 185
14. Hall, B.; Bird, R. R.; Kojima, M.; Chapman, D., Biomaterials, 1989, 10, 445
15. Ward, R. S.; White, K. A.; Hu, C. B.; Polyurethanes in Biomedical Engineering, 1984, 181
16. Society for Biomaterials—20th Annual Meeting, April 5–9, 1994, Boston, Mass., U.S.A.; and references cited therein.
17. Tang, Y. -W.; Santerre, J. P., Labow, R. S., Waghray, G., Taylor, D. The Use of Surface Modifying Macromolecules to Inhibit Biodegradation of Segmented Polyurethanes. 20th Annual Meeting of the Society for Biomaterials, Boston, Mass., U.S.A., page 62 (1994).
18. Ito Y.; lwata, K.; Kang, 1. K.; Imanishi, Y., "Synthesis, Blood Compatibility and Gas Permeability of Copolypeptides Containing Fluoroalkyl Side Groups", Int. J. Biol. Macromol., 1988, 10, 201–208
19. Han, P. K.; Yong, S. Y.; Kim, Y. H.; Min, B. G., "Surface Characteristics and Blood Compatibility of Polyurethanes Grafted by Perfluoroalkyl Chains", J. Biomater. Sci. Polym. Ed., 1992, 3(3), 229–241
20. Budavari, S.; O'Neil, M. J.; Smith, A.; Keckelinan, P. E., Eds., "The Merck Index: An Encyclopedia of Chemicals, Drugs, and Biological", Merk & Co., Inc., Rahway, N.J., U.S.A. 1989

SUMMARY OF THE INVENTION

It is an object of the present invention to provide polymer composition of fluoroalkyl surface-modifying macromolecules in admixture with a compatible base elastomer for providing improved surface properties to an article.

It is a further object of the present invention to provide polymer compositions of fluoroalkyl surface-modifiing macromolecules in admixture with a base polyurethane elastomer for use as medical implant devices having improved stability and acceptable blood compatibility.

It is a further object of the invention to provide said articles, particularly, said medical implant devices.

It is a further object of the invention to provide novel fluoroalkyl surface-modifying macromolecules of use in said polymer compositions.

It is a further object of the invention to provide fluoroalcohols of use in the preparation of said fluoralkyl surface-modifying macromolecules.

It is a further object of the invention to provide processes of manufacture of said fluoroalkyl surface-modifying macromolecules.

Accordingly, in one aspect the invention provides a surface modifying macromolecule having a central portion and terminal groups, the central portion being a member selected from the group consisting of a soft central portion and a hard central portion, the central portion having a molecular weight of less than 5,000 and including a segmented oligomeric copolymer unit including at least one polar segment and at least one hydrophobic segment, and the terminal groups including $\alpha$-$\omega$ terminal polyfluoro oligomeric groups. Preferably the oligomeric copolymer unit has a molecular weight of less than 5000, e.g. less than 2000 such as 200–1200.

The amphipatic surface modifying macromolecule is sometimes denoted as "SMM"in this specification.

By the term "segmented" is meant a relatively short length of a repeating unit, generally less than about 10 monomeric units having, preferably, structural formulas such as ABAB, wherein A represents a polar hard segment chemically bonded to a soft block B.

Preferably, the polyfluoro oligomeric group is a perfluoroalkyl group; and the polar hard segment is selected from the group consisting of a urethane, ester, amide, sulfonamide and carbonate.

In a further aspect, the invention invention provides a shaped article of a base polymer in admixture with a surface modifying macromolecule having a central portion and terminal groups, , the central portion being a member selected from the group consisting of a soft central portion and a hard central portion, the central portion having a molecular weight of less than 5,000 and including a segmented oligomeric copolymer unit including at least one polar segment and at least one hydrophobic segment, and the terminal groups including $\alpha$-$\omega$ terminal polyfluoroalkyl oligomeric groups.

Examples of typical base polymers of use in admixture with aforesaid SMM according to the invention includes polyurethanes, polysulfones, polycarbonates, polyesters, polyethylene, polyproprylene, polystyrene, poly (acrylonitrile-butadienestyrene), polybutadiene, polyisoprene, styrenebutadiene-styrene block copolymers, styrene-isoprenestyrene block copolymers, poly-4-methylpentene, polyisobutylene,polymethyl-methacrylate, polyvinylacetate, polyacrylonitrile, polyvinyl chloride, polyethylene terephthalate, cellulose and its esters and derivatives Preferred segmented polymers include polyurethanes, polyester, polyethers, polyether-polyamides and polyamides.

The admixed compositions according to the invention may be used as a surface covering for an article, or, most preferably, where the composition comprises a base polymer of a type capable of being formed into a self-supporting structural body, film, or woven or knit as a fiber, as a surface or in whole or in part of the article, preferably, a biomedical device or component thereof.

In a preferred aspect the invention provides a composition comprising in admixture a polyurethane elastomer and a compatible surface-modifying macromolecule in a surface-modifying enhancing amount, wherein said polyurethane elastomer has a molecular weight of at least 1.05 times the molecular weight of said SMM.

In this specification:

| | |
|---|---|
| SMM - | surface modifying macromolecule |
| MDI - | methylene diphenyl diisocyanate |
| HDI - | 1,6-Hexanediisocyanate |
| PPO - | polypropylene oxide diol |
| TDI - | 2,4-toluene diisocyanate |
| PCL - | polycaprolactone diol |
| ED - | ethylenediamine |
| PTMO - | polytetramethylene oxide diol |

BA:
BA-L (low boiling point fraction)
BA-L (intermediate boiling fraction) and
BA-L (high boiling fraction)

Thus, this invention, in one aspect, describes a family of novel amphipathic surface modifying macromolecules that have fluorinated tails at the ends of the polymer chain. The centre of the SMM chain is tailored to be compatible with the base polymer substrate to which the SMM is added.

The SMM's, according to the invention, are synthesized in a manner that they contain a base polymer compatible segment and terminal hydrophobic fluorine components which are non-compatible with the base polymer. The compatible segment of the SMM is selected to provide an anchor for the SMM within the base polymer substrate upon admixture. While not being bound by theory, it is believed that the fluorine tails are responsible in part for carrying the SMM to the surface of the admixture, with the chemical resistant fluorine chains exposed out from the surface. The latter process is believed to be driven by the thermodynamic incompatibility of the fluorine tail with the polymer base substrate, as well as the tendency towards establishing a low surface energy at the mixture's surface. When the balance between anchoring and surface migration is achieved, the SMM remains stable at the surface of the polymer, while simultaneously altering surface properties. The utility of the additives of the invention versus other known macromolecular additives, lies in 1) the molecular arrangement of the amphipathic segments in the SMM chain, i.e. two -ω fluoro-tails, one at each end, with the polar segment sandwiched between them; 2) the molecular weight of the fluorine tails relative to that of the central segment and; 3) the ability of the materials to inhibit biodegradation of the base polymer when the fluoro-segments are stabilized at the interface, which provides improved blood compatibility and biostability of the base polymers. This latter improvement has not been previously achieved and/or demonstrated with any other family of amphipathic polymeric type surface modifying macromolecules.

The surface modifying macromolecules according to the invention significantly alter the surface chemistry of, for example, segmented polyurethanes, i.e. the SMMs migrate to the surface of the polymer mixture and exhibit a new hydrophobic surface. The advancing and receding contact angles for the examples hereinafter described show significant increases and parallel values for contact angles obtained for pure Teflon® (116° for advancing contact angle and 92° for receding contact angle). Simultaneously, the thermal transitions of polyurethane base polymers containing the SMM do not change with the addition of 5% SMM into the base polyurethanes. This implies that the polyurethanes retain most of the structure which defines their elastomeric nature, but yet have surface characteristics similar to Teflon®. This new surface carries many of the attributes of perfluoro-carbon chains and, therefore, is significantly more stable with respect to oxidation and hydrolysis than many polyurethanes. Further, the surface has low fouling properties and low wetting characteristics.

The SMM's are, for example, of use with linear or crosslinked polyurethane-based materials. By tailoring the central segment components of the SMM, the invention can be applied inter alia to a wide range of polymer materials which include polymers synthesized with reagents that are of common knowledge in the field of polyurethanes. These include, but are not limited to, the diisocyanates, soft segment components and chain extenders listed below:

Common Reagents for Polyurethane Synthesis

| DIISOCYANATES | SOFT SEGMENT PRECURSOR COMPONENT DIOL | CHAIN EXTENDERS |
| --- | --- | --- |
| 2,4 toluene diisocyanate | polyethylene oxide | 1,4-butanediol |
| 2,6 toluene diisocyanate | polypropylene oxide | ethylene diamine |
| methylene bis(p-phenyl) diisocyanate | polyetramethylene oxide | 4,4' methylene |
| 1,5 naphthanene diisocyanate | polyisobutylene | bis(2-chloroaniline) |
| 3,3' bitoluene diisocyanate | polybutadienes | ethylene glycol |
| methylene bis(p-cyclohexyl isocyanate) | polyethylene adipate | hexanediol |
| 1,6 hexane diisocyanate | polytetramethylene adipate | |
| 1,12 dodecane diisocyanate | polycaprolactone | |
| isophorone diisocyanate | polydimethylsiloxane | |
| cyclothexyl diisocyanate | polycarbonates | |

The term "soft segments" refers to those parts of the central segment components that are not polar hard segments.

While the reagents listed hereinabove are di-functional with respect to their reactive groups, it is understood that they could also be tri- or multi-functional. Either branched or crosslinked polyurethanes could be generated. The soft segment precursor components listed and others of similar function, can either contain hydroxy, carboxylic acid or amine reactive chemical functional groups for the isocyanates.

There are no restrictions on the specific stoichiometry of the reagents used in the synthesis of the SMM, the manner in which they are added to each other, the temperature, pressure or atmosphere under which they are synthesized or the use of catalysts in their reaction. However, the molecular weight of the soft segment of the central component is, typically, between 200 and 5000 molecular weight. It is not desirable to simultaneously synthesize a SMM additive with the base polymer to which they are admixed, since the synthesis of the SMM additive is sensitive to reaction conditions. However, the SMM additives may be added to the synthesized base polymer, immediately following the latter's synthesis, in such a manner as to incorporate the SMM additives into the base polymer substrate prior to the final work-up of the polymer substrate.

In order to illustrate the use of SMM additives with common polyurethanes as the base polymer, and to describe the rationale for the selection of the SMM candidates, two polyurethanes were synthesized from the list of reagents given, hereinbefore. One material is a polyester urea-urethane (named TDI/PCL/ED), synthesized from 2,4-toluene diisocyanate (TDI), polycaprolactone (PCL, molecular weight 1000) and ethylene diamine (ED). The other material is a polyether urea-urethane (TDI/PTMO/ED) synthesized with TDI, ED and polytetramethylene oxide (PTMO, molecular weight 1000). Both polyurethanes have a reagent weight content which is larger in soft segment component than in aromatic diisocyanate component. The soft segment of both polyurethanes has a tendency to crystallize and both the carbonyl segments of PCL and ether segments of PTMO tend to form hydrogen bonding networks with the urethane and urea groups. The crystalline character and degree of hydrogen bonding will, in most instances be greater for the TDI/PCU/ED material. Hence, the reagents and stoichiometry used in the synthesis of an SMM for these particular materials should favour hydrogen bonding interactions with base polyurethanes, in order to effectively stabilize the SMM in the admixed material for prolonged periods of time. The selection of a PTMO based soft segment for the SMM likely favours long-term stability of the SMM over a molecule like polypropylene oxide, since the latter's side chain methyl group inhibits the molecule to crystallize and reduces its ability to effectively hydrogen bond with urea and urethane groups. On the other hand, migration of a PTMO based SMM will be inhibited to a greater extent than an equivalent sized SMM synthesized with PPO, since the latter will have lower interaction forces with either of the base polymers. Therefore, the control of the molecular weight in the synthesis of an effective SMM is highly desirable in its ability to modify the surface chemistry of the polyurethane substrates.

General Synthesis of an SMM

SMM may be synthesized using a multi-functional isocyanate, a multi-functional soft segment precursor reactive therewith, and a mono function polyfluoro-alcohol. The isocyanate is preferably, but not so limited to be di-functional in nature, in order to favour the formation of a linear SMM. Linear as apposed to branched or crosslinked SMM have better migration properties within the polyurethane substrate. A preferred diisocyanate for biomedical applications is 1,6-hexanediisocyanate. The soft segment precursor molecule is preferably di-functional in nature but not so limited to be di-functional, in order to favour the formation of a linear SMM. Again, linearity favours migration properties within the base polymer substrate. Examples of typical soft segment precursors include, polypropylene oxide polyols of molecular weight 1000, and polytetramethylene oxide diols of molecular weight 1000. SMM's are synthesized using a preliminary prepolymer method similar to the classical one used for polyurethanes. However, the subsequent step differs in that a chain extension is not carried out. A mono-functional oligomeric fluorinated alcohol is used to cap the prepolymer, rather than chain extend the prepolymer. The fluorinated alcohol preferably has a single fluoro-tail but is not limited to this feature. A general formula for the oligomeric fluoro-alcohol of use in the invention is $H-(OCH_2CH_2)_n-(CF_2)_m-CF_3$, wherein n can range from 1 to 10, but preferably ranges from 1 to 4, and m can range from 1 to 20 but preferably ranges from 2 to 12. A general guide for the selection of "n" relative to "m" is that "m" should be equal or greater to "2n" in order to minimize the likelihood of the $(OCH_2CH_2)_n$ segment displacing the $(CF_2)_m-CF_3$ from the surface following exposure to water, since the former is more hydrophilic than the fluorotail and will compete with the fluorotail for the surface. Without being bound by theory, the presence of the (OCH2CH2)n segment is believed to be important to the function of the SMM because it provides a highly mobile spacer segment between the fluorotail and the substrate. This is important in order to effectively expose the fluorosurface to, for example, an aqueous medium. Examples of typical oligomeric fluoroalcohols include various fractions BA-L, BA-N, FSO-100 and FSN-100 (trade marks—otained from DuPont de Nemours, Wilmington, Del.).

SMM can be synthesized with different components and stoichiometry. Prior to synthesis, the isocyanate is, preferably, vacuum distilled to remove residual moisture. Soft segment precursors are degassed overnight to remove residual moisture and low molecular weight organics. In an example where BA-L is used as the fluoroalcohol, this reagent is fractionated into three fractions to reduce the distribution of molecules with different "m" values. This reduces the selective reaction of a fluoro-alcohol of a particular "m" value over another. The BA-L fractions were characterized as (i) a first fraction, herein called BA-L (Low) which is a clear liquid distilled at 102° C. and atmospheric pressure; (ii) a second fraction referred to as BA-L (Intermediate), which is a white semi-solid material, distilled between 70 and 80° C. under a vacuum of 0.01 mm Hg pressure; and (iii) a last fraction referred to as BA-L (High) and is distilled between 80 and 100° C. under a vacuum of 0.01 mm Hg as a very pale yellow solid. The selection of these fractions is somewhat arbitrary and it will be apparent to those skilled in the art that different fractions can be selected to alter the nature of the SMM in order to tailor the material for specific applications with base polymers.

While the reactants can be reacted in the absence of solvents, it is preferable to use organic solvents compatible with the chemical nature of the reagents in order to have good control over the characteristics of the final product. Typical organic solvents include dimethyl acetamide, acetone, tetrahydrofuran and dimethyl sulfoxide. A preferred reaction solvent is N, N-dimethylacetamide (DMAC, Aldrich Chemical Company, Milwaukee, Wis.).

In view of the low reaction activity of some diisocyanates, e.g. HDI, with soft segment precursor diols, a catalyst is preferred for the synthesis. Typical catalysts are similar to those used in the synthesis of polyurethanes and, include, dibutyltin dilaurate, stannous octoate, N,N-diethylcyclohexylamine, N-methylmorpholine, tetrarnethylbutane-dianine and 1,4 diazo (2,2,2) bicyclooctane.

In the first step of the preparation of an SMM, for example, the isocyanate is added to the soft segment component and, optionally, catalyst to provide a prepolymer. Subsequently the fluoro-alcohol is added to the prepolymer and generally the mixture allowed to react overnight. The SMM polymer is precipitated in distilled water, washed to remove any residual fluoro-alcohol and dried.

Examples and fabrication of products

The SMM's can be manipulated and handled for use with base polymers in the same manner as the polymers per se can be handled in the fabrication of article products. The SMM may be admixed with, for example, polyurethane base polymer 1) by compounding methods for subsequent extrusion or injection molding of articles; 2) by co-dissolving the polyurethane and SMM into a solvent of common compatibility for subsequent casting of an article in a mold or for spinning fibers to fabricate an article; or 3) by wetting the surface of a polyurethane with a solution of SMM in a solvent of common compatibility with the polyurethane to which the SMM solution is being applied.

The invention, thus, provides in one aspect a series of fluorine-containing oligomeric surface modifying macromolecules. When used in admixture with, for example, a polyurethane, the SMM's inhibit polyurethane degradation by enzyme action. The SMMs are copolymers or terpolymers that have the ability to alter the surface chemistry and, hence, surface properties of a polymer and are synthesized in such a manner that (i) preferably, they have a lower molecular weight than the base material i.e. the polymer that requires protection from biodegradation and (ii) they contain a surface active segment containing ($\alpha$-$\omega$ terminal polyfluoro groups.

Products such as medical devices formed of the admixed composition of the invention, have their surfaces modified as a result of the selective migration and interfacial localization of the low molecular weight oligomer macromolecule containing carbon/fluorine segments and non-carbon/fluorine segments within the same molecule, such that the carbon/fluorine segments are terminal in the macromolecule and selectively reside at the material/environment interface while the non-carbon/fluorine segments are remote from the macromolecule's terminal position but reside within the upper surface of the product.

SMMs, thus, contain, preferably as $\alpha$-w terminal groups, fluoropolymeric segments comprising a sequential group of carbon atoms containing fluorine atoms and constituting an oligomeric chain. Preferred perfluorinated alcohols of use in the practice of the invention are those of the general formula $CF_3(CF_2)_nCH_2CH_2OH$, having a linear alkyl chain, wherein n is 5–9, most preferably $C_8F_{17}CH_2CH_2OH$. These monomers are commercially available under the trademark ZONYL (du Pont de Nemours, Wilmington, Del., USA) as homologous mixtures having varying degrees of fluoralkane chain lengths. One such preferred mixture available under the name BA-L has an average molecular weight of 443; fluorine content of 70%; S.G. 1.5@30° C.; thickening point<25° C. and a boiling range of 102–175° C.@50 mm Hg.

DETAILED DESCRIPTION OF PREFERRED EMBODIMENTS

In order that the invention may be better understood, preferred embodiments will now be described by way of example only.

SMM's were synthesized using classical two-step prepolymer and end-capping reactions.

Base polymers were synthesized with, for example, polycaprolactone diol (molecular weight=1250) and 2,4-toluene diisocyanate (TDI) to produce polyurethane prepolymers and with ethylene diamine as the chain extender. Fluorinated SMMs were synthesized using HDI (1,6 Hexamethylene diisocyanate), either PPO, PCL or PTMO and a fluorinated alcohol. These materials were then combined with the base polyurethane in different concentrations to yield the final test materials. Molecular weights of the base polyurethane and the SMM were determined by gel permeation chromatography (GPC). Surface concentration of elements in the prepared materials was obtained using X-ray Photo-Electron-Spectroscopy (XPS). Elemental concentration of the SMM materials and the base polymer were obtained by analytical techniques at Guelph Chemical Laboratories.

The surface wettability was evaluated by contact angle measurements. The microstructure of the materials were examined by differential scanning calorimetry (DSC).

Base polyurethanes for enzyme degradation tests were synthesized with radiolabelled $^{14}$ED or $^{14}$TDI in order to provide materials with a sensitive marker for degradation. Biodegradation experiments were run using polymer coated tubes which were incubated in buffer (0.05 M sodium phosphate, pH7) and cholesterol esterase (CE) at 37° C. in sterile vacutainers. Polyurethane materials with and without SMMs were evaluated and the solutions were sampled for counting at defined intervals. Fresh solution was added to maintain enzyme activity and experiments were run in triplicate.

The polystyrene equivalent molecular weights of the base polyurethanes were of the order of $1 \times 10^5$, while that of the SMMs ranged from 1.0 to $5.0 \times 10^4$. Characteristics of some SMMs are described below.

| Name | Description | Molecular weight |
|---|---|---|
| PPO-322I | tacky powder | $5.0 \times 10^4$ |
| PPO-32H | elastic particles | $2.6 \times 10^4$ |
| PPO-212L | tacky powder | $2.1 \times 10^4$ |
| PTMO-212L | soft flake | $3.1 \times 10^4$ |

The description of each SMM clearly shows the flexibility in properties that the different SMMs have. It is this very same flexibility that allows the macromolecules to be tailored to their respective base polymers. Surface chemistry analysis of the base polymer after modification with SMMs (to a concentration of 5% weight/weight) has shown that the surface content of fluorine could be increased to as high as 66% atomic %. This indicates the selective migration of the SMMs to the surface.

EXAMPLE 1
HDI-PPO212L (SMM) and mixtures with TDI/PCCL/ED (Polyurethane Base Polymer)

This is an example of an SMM which contains a very high fluorine content, high order structure, has selective migration to the surface of polyurethanes and enhances the hydrolytic stability of a polyesterurethane and was synthesized with PPO diol of molecular weight 1000, 1,6-hexamethylene diisocyanate (HDI), and the low boiling fraction of the fluoroalcohol (BA-L). This SMM will be referred to as HDI-PPO-212L throughout this text. The conditions of the synthesis for this reaction were as follows. 10 grams of PPO were reacted with 3.36 grams of HDI for two hours and then 5 grams of BA-L (low boiling fraction) were added to the reaction. The mixture was reacted with 42.5 mg of the catalyst, dibutyltin dilaurate, in 130 mLs of dimethylacetamide (DMAc) and the reaction temperature for the prepolymer step was maintained within 60–70° C. The polystyrene equivalent weight average molecular weight is $1.6+/-0.2 \times 10^4$ and its total fluorine content is 18.87+/-2.38% by weight. This SMM formulation produced an additive that has characteristic structural features which enhance the material's physical stability at the surface of an elastomer infacing with an aqueous media. This characteristic structure is defined by two higher order thermal transitions at approximately 14° C. and 85° C. These thermal transitions are detectable by differential scanning calorimetry and are not associated with the PPO segment of the SMM since the latter is defined by the Tg temperature of HDI-PP0212-L, i.e. −53° C. to −47° C.

Upon admixture of HDI-PPO-212L to the polyesterurethane (TDI/PCL/ED) it was observed that this additive migrated to the surface. Evidence of this by X-ray photoelectron spectroscopy data is shown in Table 1. The addition of 1% by weight of SMM to TDI/PCL/ED generates a top 10 nm surface that is saturated with fluorine. A 1% by weight sample of HDI-PP0212L in TDI/PCl/ED contains an approximate total weight % of fluorine equal to 0.19%. Table 1 shows that within the top 2 nm (15° take-off angle) there is at least 54 atomic % (65% by weight) fluorine. This represents a 340 fold increase in fluorine concentration at the surface. Even at a depth of 10 nm (905 (1) take-off angle) there is still 47 atomic % fluorine. The actual numbers are probably even higher since it is well known that the X-rays used in the XPS technique can degrade the fluorine hydrocarbons during sample analysis. The addition of 5% SMM does not significantly change the content of fluorine at the surface, compared to 1% SMM, which would imply that at an SMM concentration of 1% of the migration of SMM molecules to the surface is as effective as it is for a material which contains 5 weight % HDI-PP0212L.

TABLE 1

XPS Data for HDI-PP0212L in TDI/PCL/ED

| HDI-PP0212L concentration in TDI/PCL/ED, wt % | Take-off Angle (degrees) | Fluorine Content (atomic %) |
|---|---|---|
| 1 | 15 | 54 |
|   | 30 | 44 |
|   | 90 | 47 |
|   | (1) |   |
| 5 | 15 | 49 |
|   | 30 | 41 |
|   | 90 | 41 |
|   | (1) |   |

While the XPS data show the migration effect, differential scanning calorimetry data indicate that the bulk polyesterurethane structure is unaltered by the presence of the HDI-PP0212L molecule since the glass transition temperature for TDI/PCL/ED with the SMM (5%) remains within the temperature range of −47° C. to −36° C., as it is for the pure TDI/PCL/ED. This further shows that the majority of SMM chains are at the surface of the polymer and not in the bulk phase, acting as a plastizer and reducing the Tg value. The physical stability of the SMM at the interface of the TDI/PCL/ED material, following exposure to water, is shown by the degree of hysteresis in the water/air contact angle data shown in Table 2. In all cases, the hysteresis values for samples containing the SMM are better or similar to that of the original polymer. This indicates that the gain in hydrophobic character that arises from the presence of the fluorine tails of the SMM is not completely displaced by the polar character of the urea and urethane chemistry, that defines the mid-section of the HDI-PP0212L (SMM) chain and the hard segment components of the polyesterurethane. The hydrophobic nature of the polyesterurethane is significantly enhanced as shown by the increase in the advancing and receding contact angle values for all concentrations of SMM.

TABLE 2

Water/air Contact Angle Data for HDI-PP0212L in TDI/PCL/ED

| HDI-PPO212L concentration in TDI/PCL/ED, wt % | Advancing contact angle (degrees) | Receding contact angle (degrees) | Hysteresis (degrees) |
|---|---|---|---|
| 0 | 77.3 +/- 0.4 | 39.6 +/- 0.6 | 36.7 +/- 0.3 |
| 1 | 98.9 +/- 0.5 | 59.9 +/- 0.9 | 38.8 +/- 1.0 |
| 2.5 | 102.5 +/- 1.2 | 75.9 +/- 1.8 | 27.2 +/- 2.1 |
| 5.0 | 109.1 +/- 1.1 | 77.2 +/- 1.3 | 29.9 +/- 1.2 |
| 7.5 | 115.3 +/- 0.5 | 78.6 +/- 0.8 | 36.2 +/- 0.8 |

The presence of HDI-PP0212L at the surface of the polyesterurethane was tested for its ability to inhibit the hydrolysis of the polymer by the enzyme, cholesterol esterase, which reflects in part the bio-environment of the long term chronic response to the body's defense mechanism against foreign bodies, such as implanted medical devices. The addition of 1% HDI-PP0212L to TDI/PCL/ED reduced the polyesterurethanes degradation by 40% over a period of 360 hours while the addition of 5% reduced degradation by about 45%. The bio-stability of the SMM in TDI/PCL/ED, as measured by the amount of radiolabelled SMM released with time in the presence of the enzyme, was excellent. No significant degradation of the SMM occurred after seven weeks of incubation with enzyme, when compared to buffer controls.

EXAMPLE 2

This next example serves to illustrate that while an SMM is optimized to inhibit hydrolytic degradation of a polyurethane with a specific chemistry, it may not perform equivalently with respect to inhibiting the hydrolytic degradation of another polyurethane with a slightly different chemistry. In this case the ester (i.e. PCL) soft segment component of the polyurethane, TDI/PCL/ED, has been substituted with an ether component, namely polytetramethylene oxide (PTMO). Upon mixing of HDI-PPO-212L to the polyetherurethane (TDI/PTMO/ED) it was observed that the additive migrated to the surface. Evidence of this was obtained from contact angle data (see Table 2) which indicated that the hydrophobic nature of the polyetherurethane was significantly enhanced and similar in magnitude as to the modified polyesterurethane material (see Table 1).

TABLE 2.1

Water/air Contact Angle Data for HDI-PPO212L in TDI/PTMO/ED

| HDI-PPO212L concentration in TDI/PCL/ED, wt % | Advancing contact angle (degrees) | Receding contact angle (degrees) | Hysteresis (degrees) |
|---|---|---|---|
| 0 | 75.0 +/- 0.8 | 50.5 +/- 1.5 | 24 +/- 2.3 |
| 1.0 | 81.0 +/- 0.8 | 53.3 +/- 0.6 | 27.4 +/- 1.4 |

TABLE 2.1-continued

Water/air Contact Angle Data for HDI-PPO212L in TDI/PTMO/ED

| HDI-PPO212L concentration in TDI/PCL/ED, wt % | Advancing contact angle (degrees) | Receding contact angle (degrees) | Hysteresis (degrees) |
|---|---|---|---|
| 2.5 | 84.4 +/- 0.6 | 54.5 +/- 0.5 | 30.3 +/- 1.1 |
| 5.0 | 95.6 +/- 1.0 | 56.3 +/- 0.8 | 39.4 +/- 1.8 |

The presence of HDI-PPO212L at the surface of the polyetherurethane is tested for its ability to inhibit the hydrolysis of the polymer by the enzyme, cholesterol esterase, which reflects in part the bio-environment of the long term chronic response to the body's defense mechanism against foreign bodies, such as implanted medical devices. The addition of 5% HDI-PPO212L to TDI/PTMO/ED did not significantly inhibit or increase the release of degradation products from this polymer, at 4 weeks. However, beyond 4 weeks there has been found to be a significant inhibition of degradation exhibited and the difference between the level of degradation for TDI/PTMO/ED versus TDI/PTMO/ED with SMM increases with time. This supports the hypothesis that the SMMs provide a longterm inhibition of degradation. This has been validated past 80 days of incubation.

In addition, it has been shown that the bio-stability of this SMM in TDI/PTMO/ED after four weeks of incubation with enzyme is approximately half as effective as it was when the same SMM was incorporated into TDI/PCL/ED (i.e. the measured radiolabelled SMM released from TDI/PTMO/ED was twice as high as that for radiolabelled SMM incorporated into TDI/PCL/ED). Since HDI-PP0212L does migrate to the surface of TDI/PTMO/ED but does not have the same ability to inhibit degradation as it did with TDI/PCL/ED it could be suggested that the chemical nature of the SMM backbone is critical in localizing the SMM exactly near or at the sites of enzyme cleavage on the polymer.

EXAMPLE 3

HDI-PTMO212L and mixtures with TDI/PCL/ED

An example of an SMM which contains a very high fluorine content but has a negative effect on the hydrolytic stability of a polyesterurethane was synthesized with PTMO diol of molecular weight 1000, 1,6-hexamethylene diisocyanate (HDI), and the low boiling fraction of the fluoroalcohol (BA-L). This SMM will be referred to as HDI-PTMO-212L throughout this text. The conditions of the synthesis for this reaction were as follows. 10 grams of PTMO were reacted with 3.36 grams of HDI for two hours and then 9 grams of BA-L (low boiling fraction) were added to the reaction. The mixture was reacted with 60 mL of the catalyst, dibutyltin dilaurate, in 70 mL of dimethylacetamide (DMAc) and the reaction temperature for the prepolymer step was maintained within 60–70° C. The polystyrene equivalent weight average molecular weight is $3.0 \times 10^4$ and its total fluorine content is 7.98% by weight.

The addition of HDI-PTMO212L into the polyesterurethane, TDI/PCL/ED, was tested for its ability to inhibit the hydrolysis of the polymer by the enzyme, cholesterol esterase. The addition of 1 and 2.5% HDI-PTMO212L to TDI/PCL/ED increased the polyesterurethane's degradation, by 80% for 2.5% by weight and 40% for 1% by weight, over a period of 360 hours. The increase in biodegradation has been attributed to an incompatibility of the SMM with the polyesterurethane. Upon casting the polymer with HDI-PTMO212L is was very difficult to achieve conditions under which a smooth continuous film could be formed.

EXAMPLE 4
HDI-PTMO2121 and mixtures with TDI/PCL/ED

This example shows the importance of controlling the synthesis reaction during the SMM formation. The simple addition of a diisocyanate, oligomeric diol and the fluorinated alcohol is not sufficient to generate an SMM with a desired molecular weight and fluorine content to allow for simultaneous surface migration, integration with the base polymer, surface stability and ultimate biostability and biocompatibility. The use of the oligomeric diol, PTMO, often resulted in prepolymer reactions that were favoured over the end capping reaction of BA-L. This was particularly apparent when reactant solvent volumes were low. This occurs in part as a result of the higher reactivity of HDI with PTMO as compared to other diols such as PPO and believed to be due to the difficulty of the hydrophobic fluorine tail to find the reactive diisocyanate sites within the prepolymer when the polarity of the prepolymer is strong (i.e. PTMO segments contribute to a more polar character than do PPO segments). HDI-PTMO2121 was synthesized with PTMO diol of molecular weight 1000, 1,6-hexamethylene diisocyanate (HDI), and the intermediate boiling fraction of the fluoroalcohol (BA-L). The conditions of the synthesis for this reaction were as follows. 5 grams of PTMO were reacted with 1.68 grams of HDI for two hours and then 4.5 grams of BA-L (intermediate boiling fraction) were added to the reaction. The mixture was reacted with 40 mL of the catalyst, dibutyltin dilaurate, in 60 mLs of dimethylacetamide (DMAc) and the reaction temperature for the prepolymer step was maintained within 60–70° C. The polystyrene equivalent weight average molecular weight is $1.4 \times 10^5$ and its total fluorine content is 0.10% by weight.

The addition of HDI-PTMO212I into the polyesterurethane, TDI/PCL/ED, was tested for its ability to inhibit the hydrolysis of the polymer by the enzyme, cholesterol esterase. The addition of 1% HDI-PTMO212I to TDI/PCL/ED does not significantly increase or decrease the polyesterurethane's degradation, however the addition of 2.5 and 5.0% by weight to the polyesterurethane significantly increases the amount of degradation products produced in the presence of enzyme by 33% over a period of 360 hours.

EXAMPLE 5
HDI-PTMO212H and mixtures with TDI/PCL/ED

A further example of the effect shown in Example 4 was also observed for HDI-PTMO212H. HDI-PTMO212H synthesized with PTMO diol of molecular weight 1000, 1,6-hexamethylene diisocyanate (HDI), and the high boiling fraction of the fluoroalcohol (BA-L). The conditions of the synthesis for this reaction were as follows. 5 grams of PTMO were reacted with 1.68 grams of HDI for two hours and then 4.5 grams of BA-L (high boiling fraction) were added to the reaction. The mixture was reacted with 40 mL of the catalyst, dibutyltin dilaurate, in 60 mLs of dimethylacetamide (DMAc) and the reaction temperature for the prepolymer step was maintained within 60–70° C. The polystyrene equivalent weight average molecular weight is $9.7 \times 10^4$ and its total fluorine content is 0.72% by weight.

The addition of HDI-PTMO212H into the polyesterurethane, TDI/PCUED, was tested for its ability to inhibit the hydrolysis of the polymer by the enzyme, cholesterol esterase. The addition of 1 and 2.5% HDI-PTMO212H to TDI/PCL/ED increased the polyesterurethane's degradation, by approximately 12% for 1% by weight and 25% for 2.5% by weight, over a period of 360 hours.

EXAMPLE 6
HDI-PP0322I and mixtures with TDI/PCI/ED

Another PPO based system in addition to Example 1 which shows preferred performance is HDI-PP0322I. This material is similar to Example 1 except that it was synthesized with a different reactant stoichiometry and contains a fluoroalcohol with a different chain length. HDI-PP0322I was synthesized with PPO diol of molecular weight 1000, 1,6-hexamethylene diisocyanate (HDI), and the intermediate boiling fraction of the fluoroalcohol (BA-L). The conditions of the synthesis for this reaction were as follows. 10 grams of PPO were reacted with 2.52 grams of HDI for two hours and then 9 grams of BA-L (intermediate boiling fraction) were added to the reaction. The mixture was reacted with 42.5 mg of the catalyst, dibutyltin dilaurate, in 130 mLs of dimethylacetamide (DMAc) and the reaction temperature for the prepolymer step was maintained within 60–70° C. The polystyrene to equivalent weight average molecular weight is $3.3 +/- 0.4 \times 10^4$ and its total fluorine content is $9.37 +/- 1.70\%$ by weight. Unlike HDI-PP0212L, this SMM formulation produced an additive that shows no higher order structures in addition to the glass transition temperature which is recorded between −54 and −48° C. This thermal transition is detectable by differential scanning calorimetry and is associated with the PPO segment of the SMM.

Upon mixture of HDI-PPO-3221 to the polyesterurethane (TDI/PCL/ED) it was observed that this additive migrated to the surface as shown by the X-ray photoelectron spectroscopy data in Table 3. The addition of 1% by weight of SMM to TDI/PCL/ED generates a top 10 nm surface that is saturated with fluorine. A 1% by weight sample of HDI-PP0322I in TDI/PCL/ED contains an approximate total weight % of fluorine equal to 0.09%. Table 3 shows that within the top 2 nm (15O take-off angle) there is at least 53 atomic % (64% by weight) fluorine. This represents a 711 fold increase in fluorine concentration at the surface. Even at a depth of 10 nm (90° (1) take-off angle) there is still 39 atomic % fluorine. The actual numbers are probably even higher since it is well known that the X-rays used in the XPS technique can degrade the fluorine hydrocarbons during sample analysis. The addition of 5% SMM does not significantly change the content of fluorine at the surface when compared to 1% SM, which would imply that at an SMM concentration of 1% the migration of SMM molecules to the surface is as effective as it is for a material which contains 5 weight % HDI-PP0322I.

TABLE 3

XPS Data for HDI-PP0322I in TDI/PCL/ED

| HDI-PPO322I concentration in TDI/PCL/ED, wt % | Take-off Angle (degrees) | Fluorine Content (atomic %) |
|---|---|---|
| 1 | 15 | 53 |
|   | 30 | 40 |
|   | 90 (I) | 39 |
| 5 | 15 | 53 |
|   | 30 | 39 |
|   | 90 (I) | 39 |

While the XPS data show the migration effect, differential scanning calorimetry data indicated that the bulk polyesterurethane structure is unaltered by the presence of the HDI-PP03221 molecule since the glass transition temperature for TDI/PCL/ED with the SMM (5%) remains within the temperature range of −47° C. to −36° C., as it is for the pure material. This further indicates that the majority of SMM chains are at the surface of the polymer and not in the bulk phase, acting as a plasticizer and reducing the Tg value. The physical stability of the SMM at the interface of the TDI/PCL/ED material, following exposure to water, is shown by the degree of hysteresis in the water/air contact angle data given in Table 4. In contrast with Example 1, the hysteresis values for samples containing HDI-PP0322I were significantly higher than that of the original TDI/PCL/ED. This indicates that the gain in hydrophobic character that arises from the presence of the fluorine tails of the SMM is significantly displaced by the polar character of the urea and urethane chemistry, that defines the mid-section of the HDI-PP0322I chain and the hard segment components of the polyesterurethane. However, the hydrophobic nature of the polyesterurethane is significantly enhanced as shown by the increase in the advancing and receding contact angle values for all concentrations of SMM. In fact, the advancing contact angle for this example, at 5% by weight of SMM in TDI/PCL/ED exceeds the value attained for Example 1 at the same SMM concentration. These results suggest that within the TDI/PCL/ED polymer, this particular SMM shows higher mobility (relative to Example 1) towards the surface and at the surface following blending with the base polymer. This is farther supported by the differential scanning calorimetry data which showed that no higher order structures were found, therefore indicating less constraints between the SMM molecules themselves and better chain mobility.

TABLE 4

Water/air Contact Angle Data for HDI-PP0322I in TDI/PCL/ED

| HDI-PPO322I concentration in TDI/PCL/ED, wt % | Advancing contact angle (degrees) | Receding contact angle (degrees) | Hysteresis (degrees) |
|---|---|---|---|
| 0 | 77.3 +/- 0.4 | 39.6 +/- 0.6 | 36.7 +/- 0.3 |
| 1 | 98.9 +/- 0.6 | 51.1 +/- 0.4 | 48.2 +/- 1.0 |
| 2.5 | 106.1 +/- 0.6 | 48.4 +/- 0.6 | 58.0 +/- 0.8 |
| 5.0 | 116.2 +/- 0.6 | 54.3 +/- 0.8 | 62.2 +/- 1.0 |
| 7.5 | 115.3 +/- 0.5 | 68.7 +/- 0.7 | 47.0 +/- 0.8 |
| 10.0 | 115.6 +/- 0.5 | 67.8 +/- 1.7 | 46.6 +/- 1.7 |

The presence of HDI-PP0322I at the surface of the polyesterurethane was tested for its ability to inhibit the hydrolysis of the polymer by the enzyme, cholesterol esterase. The addition of 1% HDI-PP0322I to TDI/PCL/ED reduced the polyesterurethane's degradation by 16% over a period of 360 hours while the addition of 5% reduced degradation by about 31%. When biodegradation was monitored for 34 weeks, the inhibition of degradation for the TDI/PCL/ED material containing 2.5% SMM was 30% and for TDI/PCL/ED containing 5% SMM the inhibition was 45%. The bio-stability of the SMM in TDI/PCL/ED, as measured by the amount of radiolabelled SMM released with time in the presence of the enzyme, was excellent. No significant degradation of SMM was observed after seven weeks of incubation with enzyme, when compared to buffer controls.

The interaction of a key protein, namely fibrinogen, involved in the blood coagulation response to biomaterials was shown to be significantly reduced (by 50% at a fibrinogen concentration of 0.01 mg/mL, 25% at a fibrinogen concentration of 0.1 mg/mL and by 15% at a fibrinogen concentration of 1.00 mg/mL). Since fibrinogen is a molecule that is crosslinked during the coagulation process and has been associated with surfaces that induce clot formation, the finding that the SMM modified surfaces reduce the amount of fibrinogen adsorption would indicate that the modified surfaces could have important blood compatibility characteristics and may reduce blood activitation in medical devices.

EXAMPLE 7

HDI-PP0322H and mixtures with TDI/PCL/ED

This material is similar to Example 6 except that was synthesized with a fluoroalcohol of a different chain length. HDI-PP0322H was synthesized with PPO diol of molecular weight 1000, 1,6-hexamethylene diisocyanate (HDI), and the high boiling fraction of the fluoroalcohol (BA-L). The conditions of the synthesis for this reaction were as follows. 10 grams of PPO were reacted with 2.52 grams of HDI for two hours and then 9 grams of BA-L (high boiling fraction) were added to the reaction. The mixture was reacted with 42.5 mg of the catalyst, dibutyltin dilaurate, in 130 mLs of dimethylacetamide (DMAc) and the reaction temperature for the prepolymer step was maintained within 60–70° C. The polystyrene equivalent weight average molecular weight is $2.9+/-0.5 \times 10^4$ and its total fluorine content is 4.63+/-2.55% by weight. Unlike Example 6, this SMM formulation produces an additive that shows higher order structures in addition to the glass transition temperature which is recorded between −54 and −49° C. These higher order transitions were consistently observed within the range of 90 to 120° C.

Upon mixture of HDI-PPO-322H to the polyesterurethane (TDI/PCL/ED) it was observed that this additive migrated to the surface. Evidence of this from the X-ray photoelectron spectroscopy data is shown in Table 5. The addition of 2.5% by weight of SMM to TDI/PCL/ED generates a top 10 nm surface that is saturated with fluorine. A 2.5% by weight sample of HDI-PP0322H in TDI/PCL/ED contains an approximate total weight % of fluorine equal to 0.11%. Table 5 shows that within the top 2 nm (15° take-off angle) there is at least 53 atomic % (64% by weight) fluorine. This represents a 582 fold increase in fluorine concentration at the surface. Even at a depth of 10 nm (90° (I) take-off angle) there is still 41 atomic % fluorine. The actual numbers are probably even higher since it is well known that the X-rays used in the XPS technique can degrade the fluorine hydrocarbons during sample analysis.

| HDI-PPO332H concentration in TDI/PCL/ED, wt % | Take-off Angle (degrees) | Fluorine Content (atomic %) |
|---|---|---|
| 2.5 | 15 | 53 |
|  | 30 | 38 |
|  | 90 (I) | 41 |

While the XPS data shows the migration effect, differential scanning calorimetry data indicate that the bulk polyesterurethane structure is unaltered by the presence of the HDI-PP0322H molecule since the glass transition temperature for TDI/PCL/ED with the SMM (5%) remains within the temperature range of −47° C. to −36° C., as it is for the pure material. This further indicates that the majority of SMM chains are at the surface of the polymer and not in the bulk phase, acting as a plasticizer and reducing the Tg value. The physical stability of the SMM at the interface of the TDI/PCL/ED material, following exposure to water, is shown by the degree of hysteresis in the water/air contact angle data given in Table 6. In contrast with Example 1, the hysteresis values for samples containing HDI-PP0322H are significantly higher than that of the original TDI/PCL/ED. This indicates that the gain in hydrophobic character that arises from the presence of the fluorine tails of the SMM is significantly displaced by the polar character of the urea and urethane chemistry, that defines the mid-section of the HDI-PP0322H chain and the hard segment components of the polyesterurethane. However, the hydrophobic nature of the polyesterurethane is significantly enhanced as shown by the increase in the advancing and receding contact angle values for all concentrations of SMM. These results show that within the TDI/PCL/ED polymer, this particular SMM shows higher mobility (relative to Example 1) towards the surface and at the surface following blending with the base polymer. This is supported by the differential scanning calorimetry data which showed that less higher order structures were found (relative to Example 1), therefore indicating less constraints between the SMM molecules themselves and better chain mobility.

TABLE 6

Water/air Contact Angle Data for HDI-PP0322H in TDI/PCL/ED

| HDI-PPO322H concentration in TDI/PCL/ED, wt % | Advancing contact angle (degrees) | Receding contact angle (degrees) | Hysteresis (degrees) |
| --- | --- | --- | --- |
| 0 | | | |
| 2.5 | 77.3 +/- 0.4 | 39.6 +/- 0.6 | 36.7 +/- 0.3 |
| | 99.9 +/- 0.6 | 56.9 +/- 0.9 | 43.1 +/- 1.0 |
| 5.0 | 110.0 +/- 0.5 | 61.7 +/- 0.3 | 50.4 +/- 0.8 |

The presence of HDI-PP0322H at the surface of the polyesterurethane was tested for its ability to inhibit the hydrolysis of the polymer by the enzyme, cholesterol esterase. The addition of 1% HDI-PP0322H to TDI/PCL/ED reduced the polyesterurethane's degradation by 30% over a period of 360 hours while the addition of 5% reduced degradation by about 45%. This SMM performs slightly better than Example 6 and similar to Example 1 over the same time frame.

EXAMPLE 8
HDI-PTMO322I and mixtures with TDI/PCL/ED

This material is similar to Example 6 except that it was synthesized with 25a different oligomeric diol. HDI-PTMO322I was synthesized with PTMO diol of molecular weight 1000, 1,6-hexamethylene diisocyanate (HDI), and the intermediate boiling fraction of the fluoroalcohol (BA-L). The conditions of the synthesis for this reaction were as follows. 10 grams of PTMO were reacted with 2.52 grams of HDI for two hours and then 9 grams of BA-L (intermediate boiling fraction) were added to the reaction. The mixture was reacted with 42.5 mg of the catalyst, dibutyltin dilaurate, in 130 mLs of dimethylacetamide (DMAc) and the reaction temperature for the prepolymer step was maintained within 60–70° C. The polystyrene equivalent weight average molecular weight is 4.6+/-0.5× $10^4$ and its total fluorine content is 5.50+/-1.21% by weight. This SMM formulation produces an additive that shows a higher order structure associated with the PTMO soft segment. Ibis indicates that a certain degree of crystallinity is likely formed in the prepolymer component of the SMM. In addition it shows a glass transition temperature which is recorded between −73 and −62° C. This latter transition is detectable by differential scanning calorimetry and is associated with the PTMO soft segment of the SMM.

Upon mixture of HDI-PTMO-322I to the polyesterurethane (TDI/PCL/ED), it was observed that this additive migrates to the surface. Evidence of this is shown by the X-ray photoelectron spectroscopy data of Table 7. The addition of 1% by weight of SMM to TDI/PCL/ED generates a top 10 nm surface that is saturated with fluorine. A 1% by weight sample of HDI-PTMO322I in TDI/PCL/ED contains an approximate total weight % of fluorine equal to 0.05%. Table 7 shows that within the top 2 nm (15 take-off angle) there is at least 53 atomic % fluorine. This represents a 1164 fold increase in fluorine concentration at the surface. Even at a depth of 10 nm (90° (1) take-off angle) there is still 38 atomic % fluorine. The actual numbers are probably even higher sine it is well known that the X-rays used in the XPS technique can degrade the fluorine hydrocarbons during sample analysis. The addition of 5% SMM does not significantly change the content of fluorine at the surface when compared to a 1% SMM content, which would imply that at an SMM concentration of 1% the migration of SMM molecules to the surface is as effective as it is for a material which contains 5 weight % HDI-PTMO322I.

TABLE 7

XPS Data for HDI-PTMO322I in TDI/PCL/ED

| HDI-PPO332I concentration in TDI/PCL/ED, wt % | Take-off Angle (degrees) | Fluorine Content (atomic %) |
| --- | --- | --- |
| 1 | 15 | 53 |
| | 30 | 39 |
| | 90 | 38 |
| | (I) | |
| 5 | 15 | 54 |
| | 30 | 39 |
| | 90 | 42 |
| | (I) | |

While the XPS data shows the migration effect, differential scanning calorimetry data indicated that the bulk polyesterurethane structure is unaltered by the presence of the HDI-PTMO322I molecule since the glass transition temperature for TDI/PCL/ED with the SMM (5%) remains within the temperature range of −47° C. to −36° C., as it is for the pure material. This further indicates that the majority of SMM chains are at the surface of the polymer and not in the bulk phase, acting as a plastizer and reducing the Tg value. The physical stability of the SMM at the interface of the TDI/PCL/ED material, following exposure to water, is shown by the degree of hysteresis in the water/air contact angle data shown in Table 8. In contrast with Examples 6 and 7, the hysteresis values for samples containing HDI-PTMO322I are significantly lower than that of the original TDI/PCL/ED. This indicates that the gain in hydrophobic character that arises from the presence of the fluorine tails of the SMM is not significantly displaced by the polar character of the urea and urethane chemistry, that defines the mid-section of the HDI-PTMO322I chain and the hard segment components of the polyesterurethane. Furthermore the degree of hysteresis is significantly improved upon the formulation presented as Example 1 and is similar to values reported for pure Teflon® (116° for advancing contact angle and 92° for receding contact angle, yielding a hysteresis of 24°) (Brandrum, J., Immugut, E. A., Eds., "Polymer Handbook", 34rd Ed., John Wiley & Sons, 1989). Simultaneously, the hydrophobic nature of the polyesterurethane is significantly enhanced as shown by the increase in the advancing and receding contact angle values for all concentrations of SMM.

TABLE 8

Water/air Contact Angle Data for HDI-PTMO322I in TDI/PCL/ED

| HDI-PTMO322I concentration in TDI/PCL/ED, wt % | Advancing contact angle (degrees) | Receding contact angle (degrees) | Hysteresis (degrees) |
|---|---|---|---|
| 0 | 77.3 +/− 0.4 | 39.6 +/− 0.6 | 36.7 +/− 0.3 |
| 1 | 94.8 +/− 0.5 | 60.9 +/− 0.6 | 33.6 +/− 0.7 |
| 2.5 | 99.1 +/− 0.2 | 68.7 +/− 0.8 | 30.4 +/− 0.9 |
| 5.0 | 107.4 +/− 0.5 | 81.4 +/− 0.6 | 25.4 +/− 0.7 |
| 7.5 | 108.9 +/− 0.4 | 81.5 +/− 0.7 | 26.9 +/− 0.8 |
| 10.0 | 112.1 +/− 0.5 | 84.2 +/− 0.6 | 27.7 +/− 0.6 |

The presence of HDI-PTMO322I at the surface of the polyesterurethane was tested for its ability to inhibit the hydrolysis of the polymer by the enzyme, cholesterol esterase. The addition of 1% HDI-PTMO322I to TDI/PCL/ED reduced the polyesterurethane's degradation by 21% over a period of 360 hours while the addition of 5% reduced degradation by about 37%. When biodegradation was monitored for 34 weeks, the inhibition of degradation for the TDI/PCL/ED material containing 5% SMM is 50%. This exceeds the performance of Example 6 and likely reflects the potential of HDI-PTMO322I to crystallize and therefore stabilize the SMM at the surface for very long periods of time. The bio-stability of the SMM in TDI/PCL/ED, as measured by the amount of radiolabelled SMM released with time in the presence of the enzyme, was excellent. No significant degradation of the SMM was observed after seven weeks of incubation with enzyme, when compared to buffer controls.

EXAMPLE 9
HDI-PTMO322H and mixtures with TDI/PCL/ED

This material is similar to Example 8 except that it was synthesized with a fluoroalcohol of a different chain length. HDI-PTMO322H was synthesized with PTMO diol of molecular weight 1000, 1,6-hexamethylene diisocyanate (HDI), and the high boiling fraction of the fluoroalcohol (BA-L). The conditions of the synthesis for this reaction were as follows. 10 grams of PTMO were reacted with 2.52 grams of HDI for two hours and then 9 grams of BA-L (high boiling fraction) were added to the reaction. The mixture was reacted with 42.5 mg of the catalyst, dibutyltin dilaurate, in 130 mLs of dimethylacetamide (DMAc) and the reaction temperature for the prepolymer step was maintained within 60–70° C. The polystyrene equivalent weight average molecular weight is $5.5+/-0.8 \times 10^4$ and its total fluorine content is 3.83+/−1.80% by weight. This SMM formulation produces an additive that shows higher order structures in addition to a glass transition temperature which is recorded between −54 and −49° C. The higher order transitions were consistently observed within the range of 70 to 120° C.

Upon mixture of HDI-PTMO-322H to the polyesterurethane (TDI/PCL/ED) it was observed that this additive migrated to the surface as shown from the X-ray photoelectron spectroscopy data given in Table 9. The addition of 1% by weight of SMM to TDI/PCL/ED generates a top 10 nm surface that is saturated with fluorine. A 1% by weight sample of HDI-PTMO322H in TDI/PCL/ED contains an approximate total weight % of fluorine equal to 0.04%. Table 9 shows that within the top 2 nm (15° take-off angle) there is at least 55 atomic % (66% by weight) fluorine. This represents a 1650 fold increase in fluorine concentration at the surface. Even at a depth of 10 nm (90° (I) take-off angle) there is still 42 atomic % fluorine. The actual numbers are probably even higher since it is well known that the X-rays used in the XPS technique can degrade the fluorine hydrocarbons during sample analysis. The addition of 5% SMM does significantly change the content of fluorine at the surface, which would imply that at an SMM concentration of 1% the migration of SM molecules to the surface is as effective as it is for a material which contains 5 weight % HDI-PTMO322H.

TABLE 9

XPS Data for HDI-PTMO322H in TDI/PCL/ED

| HDI-PTM0O322H Concentration in TDI/PCL/ED, wt % | Take-off Angle (degrees) | Fluorine Content (atomic %) |
|---|---|---|
| 1 | 15 | 55 |
|   | 30 | 42 |
|   | 90 (I) | 42 |
| 5 | 15 | 53 |
|   | 30 | 43 |
|   | 90 (I) | 45 |

While the XPS data shows the migration effect, differential scanning calorimetry data indicate that the bulk polyesterurethane structure is unaltered by the presence of the HDI-PTMO322H molecule since the glass transition temperature for TDI/PCL/ED with the SMM (5%) remains within the temperature range of −47° C. to −36° C., as it is for the pure material. This further indicates that the majority of SMM chains are at the surface of the polymer and not in the bulk phase, acting as a plastizer and reducing the Tg value. The physical stability of the SMM at the interface of the TDI/PCL/ED material, following exposure to water, is shown by the degree of hysteresis in the water/air contact angle data shown in Table 10. In contrast with Examples 6 and 7, the hysteresis values for samples containing HDI-PTMO322H are significantly lower than that of the original TDI/PCL/ED. This indicates that the gain in hydrophobic character that arises from the presence of the fluorine tails of the SMM is not significantly displaced by the polar character of the urea and urethane chemistry, that defines the midsection of the HDI-PTMO322H chain and the hard segment components of the polyesterurethane. Furthermore the degree of hysteresis is significantly improved upon the formulation presented in Examples 1 and 8, and even surpasses the value reported for pure Teflon® (116° for advancing contact angle and 920 for receding contact angle, yielding a hysteresis of 24°). Simultaneously, the hydrophobic nature of the polyesterurethane is significantly enhanced as shown by the increase in the advancing and receding contact angle values for all concentrations of SMM.

TABLE 10

Water/air Contact Angle Data for HDI-PTMO322H in TDI/PCL/ED

| HDI-PTMO322H concentration in TDI/PCL/ED, wt % | Advancing contact angle (degrees) | Receding contact angle (degrees) | Hysteresis (degrees) |
|---|---|---|---|
| 0 | 77.3 +/− 0.4 | 39.6 +/− 0.6 | 36.7 +/− 0.3 |
| 2.5 | 113.8 +/− 0.4 | 99.4 +/− 0.3 | 14.4 +/− 0.5 |
| 5.0 | 115.6 +/− 0.4 | 105.2 +/− 0.6 | 10.4 +/− 0.8 |

The presence of HDI-PTMO322H at the surface of the polyesterurethane was tested for its ability to inhibit the hydrolysis of the polymer by the enzyme, cholesterol esterase. The addition of 1% HDI-PTMO322H to TDI/PCL/ED reduced the polyesterurethane's degradation by 38% over a period of 360 hours while the addition of 5% reduced degradation by about 40%. This SMM performs slightly better than Example 7 and similar to Example 1 over the same time frame.

EXAMPLE 10

HDI-PTMO322L and mixtures with TDI/PCL/ED

A further example of the effect shown in Example 4 was also observed for HDI-PTMO322L. HDI-PTMO322L was synthesized with PTMO diol of molecular weight 1000, 1,6-hexamethylene diisocyanate (HDI), and the low boiling fraction of the fluoroalcohol (BA-L). The conditions of the synthesis for this reaction were as follows. 10 grams of PTMO were reacted with 2.52 grams of HDI for two hours and then 5.0 grams of BA-L (low boiling fraction) were added to the reaction. The mixture was reacted with 60 µL of the catalyst, dibutyltin dilaurate, in 70 mLs of dimethyl-acetamide (DMAc) and the reaction temperature for the prepolymer step was maintained within 60–70° C. The polystyrene equivalent weight average molecular weight is $2.4 \times 10^5$ and no fluorine was detected. No further testing of this material was carried out since it represented a failed synthesis, based on the need to obtain materials with a measurable presence fluorine and molecular weights lower than that of typical polyurethanes.

EXAMPLE 11

HDI-PTMO432L and mixtures with TDI/PCL/ED

At SMM stoichiometries of 4:3:2 for diisocyanate:oligomeric diol:fluoroalcohol respectively it becomes difficult to control the prepolymer reaction over the fluoroalcohol attachment reaction. Consequently, the molecular weights can become quite large and the ability to incorporate fluorine into the SMM difficult. This lack of control is particularly apparent when the reactant concentrations are high or the reactant solvent volume is low. The following example illustrates this aspect of the SMM synthesis. HDI-PTMO432L was synthesized with PTMO diol of molecular weight 1000, 1,6-hexamethylene diisocyanate (HDI), and the low boiling fraction of the fluoroalcohol (BA-L). The conditions of the synthesis for this reaction were as follows. 10 grams of PTMO were reacted with 2.24 grams of HDI for two hours and then 4.0 grams of BA-L (low boiling fraction) were added to the reaction. The mixture was reacted with 100 µL of the catalyst, dibutyltin dilaurate, in 70 mLs of dimethyl-acetamide (DMAc) and the reaction temperature for the prepolymer step was maintained within 60–70° C. The polystyrene equivalent weight average molecular weight is $1.8 \times 10^5$ and no fluorine was detected.

It is recognized that the fluorine analysis method for the pure SMM has limitations since it can only measure ppm levels of fluorine. If the SMM is concentrated at the surface then even SMM containing concentrations of fluorine in the ppm range could theoretically migrate to the surface and show a detectable amount of fluorine using the X-ray photo-electron spectroscopy (XPS) methods. For this reason XPS analysis of the top 10 nm of the surface was carried out. A fluorine concentration of 3.38 atomic % was detected. This very low concentration of fluorine reflects the nature of the SMM and confirms the absence of a significant SMM surface modification. No further testing of this material was carried out since it represented a failed synthesis, based on the need to obtain materials with an elevated fluorine content and molecular weights lower than that of typical polyurethanes.

EXAMPLE 12

HDI-PTMO4321 and mixtures with TDI/PCL/ED

A further demonstration of the effect shown in Example 11 was also observed for HDI-PTMO432–1. HDI-PTMO4321 was synthesized with PTMO diol of molecular weight 1000, 1,6-hexamethylene diisocyanate (HDI), and the intermediate boiling fraction of the fluoroalcohol (BA-L). The conditions of the synthesis for this reaction were as follows. 10 grams of PTMO were reacted with 2.24 grams of HDI for two hours and then 4.0 grams of BA-L (intermediate boiling fraction) were added to the reaction. The mixture was reacted with 80 µL of the catalyst, dibutyltin dilaurate, in 70 mLs of dimethyl-acetamide (DMAc) and the reaction temperature for the prepolymer step was maintained within 60–70° C. The polystyrene equivalent weight average molecular weight is $1.1 \times 10^5$ and no fluorine was detected.

XPS analysis of the surface was carried out in the same manner as for Example 11. It was found that the top 10 nm of the surface contained 4 atomic % fluorine. No further testing of this material was carried out since it represented a failed synthesis, based on the need to obtain materials with an elevated fluorine content and molecular weights lower than that of typical polyurethanes.

EXAMPLE 13

HDI-PTMO432H and mixtures with TDI/PCL/ED

It was stated in Example 11 that solvent volume, which determines reactant concentrations, was important for the control of the SMM synthesis. The following example illustrates this. By increasing the reactant solvent volume, an SMM synthesized from similar reactants to those used in Examples 11 and 12 can be produced with properties that more appropriately match the desired character of the SMM's.

HDI-PTMO432H was synthesized with PTMO diol of molecular weight 1000, 1,6-hexamethylene diisocyanate (HDI), and the high boiling fraction of the fluoroalcohol (BA-L). The conditions of the synthesis for this reaction were as follows. 10 grams of PTMO were reacted with 2.24 grams of HDI for two hours and then 4.0 grams of BA-L (high boiling fraction) were added to the reaction. The mixture was reacted with 80 µL of the catalyst, dibutyltin dilaurate, in 100 mLs (as compared to 70 mLs for Examples 10 and 11) of dimethyl-acetamide (DMAc) and the reaction temperature for the prepolymer step was maintained within 60–70° C. The polystyrene equivalent weight average molecular weight is $7.1 \times 10^4$ and the fluorine content was 3.28 wt %.

Upon mixture of HDI-PTMO432H to the polyesterurethane (TDI/PCL/ED) it was observed that this additive migrates to the surface as shown by the X-ray photoelectron spectroscopy data of Table 11. The addition of 5% by weight of SMM to TDI/PCUED generates a top 10 nm surface that is saturated with fluorine. Table 11 shows that within the top 2 nm (20° take-off angle) there is at least 57 atomic % fluorine. Even at a depth of 10 nm (900 (I) take-off angle) there is still 44 atomic % fluorine. Therefore the fluorine content at the immediate surface is similar in concentration to the preferred formulations presented in Examples 1, 2, 6, 7, 8 and 9.

TABLE 11

XPS Data for HDI-PTMO432H in TDI/PCL/ED

| HDI-PTMO432H concentration in TDI/PCL/ED, wt % | Take-off Angle (degrees) | Fluorine Content (atomic %) |
|---|---|---|
| 5 | 20 | 57 |
|   | 45 | 47 |
|   | 90 | 44 |
|   | (I) |   |

The addition of HDI-PTMO432H into the polyesterurethane, TDI/PCL/ED, was tested for its ability to inhibit the hydrolysis of the polymer by the enzyme, cholesterol esterase. The addition of 1% HDI-PTMO432H to TDI/PCL/ED does not significantly increase or decrease the polyesterurethane's degradation, however the addition of 2.5% by weight to the polyesterurethane significantly increases the amount of degradation products produced in the presence of enzyme by 18%, over a period of 360 hours.

EXAMPLE 14

MDI-PPO(425)322H

This example illustrates that the SMMs can be synthesized from various diisocyanates (differing from HDI) and oligomeric diols differing in molecular weight from 1000. An example of an SMM which contains a very high fluorine content was synthesized with PPO diol of molecular weight 425, 4,4'-methylene diphenyl-diisocyanate (MDI), and the high boiling fraction of the fluoroalcohol (BA-L). This SMM is referred to as MDI-PPO(425)322H throughout this text. The conditions of the synthesis for this reaction were as follows. 8.5 grams of PPO were reacted with 7.5 grams of MDI for two hours and then 11.78 grams of BA-L (high boiling fraction) were added to the reaction. The mixture was reacted without catalyst in 100 mLs of dimethylacetamide (DMAc) and the reaction temperature for the prepolymer step was maintained within 60–70° C. The polystyrene equivalent weight average molecular weight is $2.7+/-0.27 \times 10^4$ and its total fluorine content is $13+/-2.00\%$ by weight. This SMM has a Tg temperature range of 17° C. to 33° C. This high Tg indicates that it is a much more rigid macromolecule than Examples 1 to 13 and is well suited for incorporation into the crystalline segments of polyurethane elastomers.

EXAMPLE 15

Examples of biomedical articles that integrate the SMM to the polyurethane using aforesaid method 1) described above include the following articles that are in whole or in part made of polyurethane components or contain some polyurethane components, namely, cardiac assist devices, cardiac replacement devices, cardiac septal patches, intra-aortic balloons, percutaneous cardiac assist devices, extracorporeal circuits, A-V fistual, dialysis components (tubing, filters, membranes, etc.), aphoresis units, membrane oxygenator, cardiac by-pass components (tubing, filters, etc.), pericardial sacs, contact lens, cochlear ear implants, sutures, sewing rings, cannulas, contraceptives, syringes, o-rings, bladders, penile implants, drug delivery systems, drainage tubes, pacemaker leads insulators, heart valves, blood bags, coatings for implantable wires, catheters, vascular stents, angioplasty balloons and devices, bandages, heart massage cups, tracheal tubes, mammary implant coatings, artificial ducts, craniofacial and maxillofacial reconstruction applications, ligaments, fallopian tubes.

Non-biomedical articles fabricated by method one would include, extruded insulation for electrical wires, o-rings and syringes.

EXAMPLE 16

Examples of biomedical articles that integrate the SMM to the polyurethane using method 2) described above include the following articles that are wholly or in part made of polyurethane components or contain some polyurethane components, namely, cardiac assist devices, cardiac replacement devices, cardiac septal patches, intra-aortic balloons, percutaneous cardiac assist devices, pericardial sacs, contact lens, sutures, cannulas, contraceptives, gloves, bladders, penile implants, drug delivery systems, drainage tubes, pacemaker leads insulators, heart valves, blood bags, coatings for implantable wires, vascular stents, angioplasty balloons and devices, bandages, heart massage cups, tracheal tubes, mammary implant coatings, artificial ducts, craniofacial and maxillofacial reconstruction applications, ligaments. Specific examples of articles within this group were prepared with 9 different SMM formulations dissolved in N, N-dimethylacetamide with the polyurethane, TDI/PCL/ED, and cast into the form of cast sheets and tubes. The flat sheets were characterized for surface composition while the tubes were used in biodegradation tests.

Non-medical applications that are exemplified by method 2) include gloves and articles of clothing made of polyurethane fibres (e.g. Lycra®).

EXAMPLE 17

Examples of biomedical articles that integrate the SMM to the polyurethane using method 3 described hereinabove, include the following articles that are in whole or in part made of polyurethane components or contain some polyurethane components: cardiac assist devices, cardiac replacement devices, cardiac septal patches, intra-aortic balloons, percutaneous cardiac assist devices, extracorporeal circuits, A-V fistual, dialysis components (tubing, filters, membranes, etc.), aphoresis units, membrane oxygenator, cardiac by-pass components (tubing, filters, etc.), pericardial sacs, contact lens, cochlear ear implants, sutures, sewing rings, cannulas, contraceptives, gloves, syringes, o-rings, bladders, penile implants, drug delivery systems, drainage tubes, pacemaker leads insulators, heart valves, blood bags, coatings for implantable wires, catheters, vascular stents, angioplasty balloons and devices, bandages, heart massage cups, tracheal tubes, mammary implant coatings, artificial ducts, craniofacial and maxillofacial reconstruction applications, ligaments, fallopian tubes.

Non-medical applications of this type include varnishes for floors and other articles as well as water repellent coatings. The properties of the SMM of the invention relate to their non-wetting and water repellent properties, as evidenced by the contact angle data given in the examples and lubricating and low adherence properties, as evidenced by the reduced protein adsorption studies for PPO-322I.

EXAMPLE 18

HDI-PTMO212I synthesized with excess fluoroalcohol and mixtures with the commercial polyurethane Tecoflex 65D EG This example shows the importance of controlling the synthesis reaction during the SMM formation, in order to achieve a desired SMM formulation. Competitive reactions of the PTMO and the fluoroalcohols with the diisocyanate chain can be minimized by using excess fluoroalcohols and ensuring that the prepolymer stage is almost complete prior to the addition of fluoroalcohols. HDI-PTMO212I is synthesized with PTMO diol of molecular weight 1000, 1,6- hexamethylene diisocyanate (HDI), and a 25% excess of the stoichiometric requirement, by weight, for the intermediate boiling fraction of the fluoroalcohol (BA-L). The conditions of the synthesis for this reaction were as follows. 16.6 grams of PTMO were reacted with 5.6 grams of HDI for four hours and then 18.5 grams of BA-L (intermediate boiling fraction) were added to the reaction. The mixture was reacted with 0.3 grams of the catalyst, dibutyltin dilaurate, in 300 mLs of dimethyl-acetamide (DMAc) and the reaction temperature for the prepolymer step was maintained within 65–70° C. The polystyrene equivalent weight average molecular weight is $2.2 \times 10^4$ and its total fluorine content is 20% by weight.

Upon admixture of this formulation of HDI-PTMO212I into the commercial polyurethane Tecoflex 65D EG (from Thermedics Inc.) it was observed that this additive migrated to the surface of the material. Tecoflex 65D EG is a polymer made from methylelene di-cyclohexane diisocyanate, polytetramethylene oxide of molecular weight 1000 and butane diol. It is an extrudable grade polymer and differs significantly from the polymers TDI/PTMO/ED and TDI/PCL/ED. In addition to the differences in chemistry it has a surface active hydrocarbon which enhances slipping properties in extruded components. Therefore the incorporated SMM in this polymer must compete for surface presence over the hydrocarbon additive. The contact angle data for the material with and without SMM illustrate that the SMMs dominate the chemistry of the modified material (see Table 12).

TABLE 12

Water/air Contact Angle Data for HDI-PTMO212I in Tecoflex 65D EG

| HDI-PTMO212I concentration in Tecoflex 65D, wt % | Advancing contact angle (degrees) | Receding contact angle (degrees) | Hysteresis (degrees) |
| --- | --- | --- | --- |
| 0 | 78.0 +/– 2 | 55 +/– 1 | 23 |
| 2.4 | 114 +/– 1 | 66 +/– 1 | 48 |
| 4.5 | 114 +/– 1 | 62 +/– 1 | 51 |

The biostability of the SMM incorporated into Tecoflex 65D EG, as measured by the amount of radiolabelled SMM released with time in the presence of enzyme and buffer is very good. Data has shown that after 4 weeks of incubation at 37° C. with enzyme there is no significant release of radiolabel above background control values. After 18 weeks there was only release of 100 counts of the original 60,000 counts in the experiment.

EXAMPLE 19

HDI-PTMO212I synthesized with excess fluoroalcohol and mixtures with the commercial polyurethane Tecoflex 80A EG This example shows that the SMM of example 18 can be incorporated into a commercial polyurethane having polymer soft segments of different length and still express a surface modification effect.

Upon admixture of HDI-PTMO2 121 from example 18 into the commercial polyurethane Tecoflex 80A EG (from Thermedics Inc.) it was observed that this additive migrated to the surface of this material. Tecoflex 85A EG is a polymer made from methylelene di-cyclohexane diisocyanate, polytetramethylene oxide of molecular weight 2000 and butane diol. It is an extrudable grade polymer and differs mechanically from Tecoflex 65D EG in its hardness. The contact angle data for the material with and without SMM illustrate that the SMMs dominate the chemistry of the modified material (see Table 13).

TABLE 13

Water/air Contact Angle Data for HDI-PTMO212I in Tecoflex 80A EG

| HDI-PTMO212I concentration in Tecoflex 80A, wt % | Advancing contact angle (degrees) | Receding contact angle (degrees) | Hysteresis (degrees) |
| --- | --- | --- | --- |
| 0 | 77 +/– 2 | 51 +/– 1 | 23 |
| 2.4 | 112 +/– 1 | 60 +/– 1 | 52 |
| 4.5 | 112 +/– 1 | 59 +/– 1 | 53 |

The biostability of the SMM incorporated into Tecoflex 80A EG, as measured by the amount of radiolabelled SMM released with time in the presence of buffer was identical to that of the 65D material (example new2) over a period of 18 weeks. In the presence of enzyme, the radiolabel release was 200 counts of the original 60,000 counts in the experiment.

EXAMPLE 20

Extruded tubing produced from the admixture of HDI-PTMO2121 (synthesized with excess fluoroalcohol) and the commercial polyurethane Tecoflex 65D EG HDI-PTMO2121 from example 18 was compounded with Tecoflex 65D EG at a concentration of 2% by weight and extruded into hollow tubing for incorporation into cardiac catheter products. Upon thermal extrusion of tubing the SMMs have migrated to the surface and express an elevated concentration of fluorine in comparison to the extruded tubing without SMM. Evidence of this is given by the XPS data, shown in Table 14. Note that the inside air dried surface expresses a significantly higher concentration of fluorine within the top 10 nm of the surface as compared to the outside surface which was quenched by water immediately following the exit of the tubing from the extruder. The water on the soft melted surface will tend to minimize the presence of the hydrophobic fluorine tails at the surface because these groups are not yet locked into the cooled structure. The water encourages the presence of the hydrophylic groups at the surface during the cooling period. This does not happen on the air cooled surface.

TABLE 14

XPS analysis of the tubing surface (top 10 nm depth)

| Sample | % atomic C | % atomic O | % atomic N | % atomic F |
| --- | --- | --- | --- | --- |
| inside tubing with SMM | 55 | 9 | 4 | 32 |
| inside tubing without SMM | 87 | 9 | 3 | 1 |
| outside tubing with SMM | 72 | 7 | 4 | 17 |
| *outside tubing without SMM | 80 | 12 | 4 | 1 |

*3% of Na and Si were found at the surface of this sample.

EXAMPLE 21

HDI-PTMO2 121 synthesized with excess fluoroalcohol and mixtures with the commercial polyurethane Corethane 80A.

This example shows that the SMM of example 18 can be incorporated into a commercial polyurethane from Corvita Inc. having polymer soft segments of different composition (i.e. polycarbonate) and still express a surface modification effect.

Upon admixture of HDI-PTMO212I from example 18 into the commercial polyurethane Corethane 80A it was observed that this additive migrated to the surface of this material. Corethane 80A is a polymer made from methylene di-phenyl diisocyanate, poly(1,6-hexyl 1,2-ethyl carbonate) diol of molecular weight 2000 and butane diol. It is an extrudable grade polymer and differs from Thermedic's Tecoflex materials in both the isocyanate chemistry and the soft segment chemistry. The contact angle data for the material with and without SMM illustrate that the SMMs dominate the chemistry of the modified material (see Table 15).

TABLE 15

Water/air Contact Angle Data for HDI-PTMO212I in Corethane 80A

| HDI-PTMO212I concentration in Corethane 80A, wt % | Advancing contact angle (degrees) | Receding contact angle (degrees) | Hysteresis (degrees) |
|---|---|---|---|
| 0 | 85 +/− 1 | 50 +/− 1 | 35 |
| 2.5 | 118 +/− 1 | 91 +/− 1 | 27 |

The surface migration of the SMM in this material is excellent and the surface hydrophobicity expressed by the surface and measured by contact angle is equivalent to that of Teflon 8.

EXAMPLE 22

Spun fibres into the shape of a hollow tube and produced from the admixture of HDI-PTMO212I (synthesized with excess fluoroalcohol) and the commercial polyurethane Corethane 80A HDI-PTMO212I from example 18 was mixed into a solution of Corethane 80A and dimethylacetamide at a concentration of 2% by weight (relative to polymer solids) and spun onto a rotating mandrel to form the shape of a hollow tube. Upon curing of the fibres on the mandrel the SMMs have migrated to the surface and express an elevated concentration of fluorine in comparison to the fibre tubing without SMM. Evidence of this is given by the XPS data, shown in Table 16. Note that the inside and outside of the hollow tube both contain elevated levels of fluorine.

TABLE 16

XPS analysis of the tubing surface

| Sample | % atomic C | % atomic O | % atomic N | % atomic F |
|---|---|---|---|---|
| inside fibre tubing with SMM | 42 | 8 | 3 | 47 |
| inside fibre tubing without SMM | 68 | 26 | 2 | 2 |
| outside fibre tubing with SMM | 42 | 8 | 3 | 46 |
| outside fibre tubing without SMM | 74 | 23 | 2 | .5 |

It was noted th at there was no qualitative distinction between the mechanical properties of the fibre tubes with or without the SMM. Hollow tubes of this nature have been used for artificial arteries and various other types of blood conduits in medical devices.

EXAMPLE 23

Synthesis of MDI-PPO(425)322FSO1

This example illustrates that the SMMs can be synthesized from various fluoroalcohols as defined herein. This particular SMM is similar to example 14 except that it was synthesized from a fluoroalcohol under the trade name of Zonyl FSO100. The latter alcohol has a similar fluorinated tail to BA-L (used in previous examples) but differs in the length of the —(CH$_2$CH$_2$O)$_n$— component, where n=1 for BA-L and n>1 for FSO-100. The latter is separated into three fractions by distillation and centrifugation processes and are defined in the following table:

| Sample | % C by weight | % F by weight | % O by weight | Chemical Formula CF$_3$(CF$_2$)$_m$(CH$_2$CH$_2$)$_n$OH | | Separation Conditions |
|---|---|---|---|---|---|---|
| FSO-100 | 36.76 | 40.35 | 18.70 | m = 8 | n = 8 | Not applicable |
| FSO1 | 31.73 | 53.97 | 11.08 | m = 8 | n = 3 | distilled 50–80° C. at 0.1 mmHg |
| FSO2 | 35.52 | 40.17 | 19.32 | m = 8 | n = 9 | distilled 80–100° C. at 0.1 mmHg |
| FSO3 | 39.77 | 36.25 | 18.78 | m = 8 | n = 10– | centrifuged and decanted |

The SMM MDI-PPO(425)322FSO1 was synthesized in the following manner. The conditions of the synthesis for this reaction were as follows. 8.5 grams of PPO were reacted with 7.5 grams of MDI for four hours and then 14.6 grams of FSO1 were added to the reaction. The mixture was reacted without catalyst in 200 mLs of dimethylacetamide (DMAc) and the reaction temperature for the prepolymer step was maintained within 40–50° C. The polystyrene equivalent weight average molecular weight is 1.7×10$^4$ and its total fluorine content is 21% by weight.

EXAMPLE 24

Synthesis of MDI-PCL(530)322L

This example illustrates that the SMMs can be synthesized from various soft segment components other than polyethers and they may be comprised of polyesters, polyamides, polysulfones etc., depending on the degree of compatibility required for the substrate in which the SMM is being added. This particular SMM is similar to example 14 except that it was synthesized from a polyester rather than a polyether, namely polycaprolactone diol. The SMM MDI-PCL(530)322L was synthesized in the following manner. The conditions of the synthesis for this reaction were as follows. 10.6 grams of PCL were reacted with 7.5 grams of MDI for four hours and then 9 grams of BA-L were added to the reaction. The mixture was reacted without catalyst in 200 mLs of dimethylacetamide (DMAC) and the reaction temperature for the prepolymer step was maintained within 40–50° C. The polystyrene equivalent weight average molecular weight is $2.6\times10^4$ and its total fluorine content is 8.6% by weight.

EXAMPLE 25

This example illustrates that the SMMs can be mixed with a range of polymers in order to achieve similar effects as to those observed for the polyurethane examples above. This is supported by the fact that in the above polyurethane examples, the dominant component, by weight %, is the soft segment chemistry. The above sited base polyurethane soft segments included polyesters, polyethers and polycarbonates. Upon optimization of SMM chemistry, these additives were shown to migrate through rigid and elastomeric polyether, polyester and polycarbonate based polyurethanes. It can therefore be implied that the SMMs can migrate through polymers ranging in composition and include but are not limited to polyesters, polyurethanes, polysulfones, polyamides, polyethers, polycarbonates, polyolefins, etc. To illustrate this, the following example is provided. The SMMs synthesized in examples 14, 23 and 24 in admixture with the commercial polyethersulfone (Victrex 4800P supplied by ICI) were cast as films from 25 wt % solutions of PES and 4% wt % SMM (relative to PES). Victrex 4800P is a rigid glassy polymer with a glass transition temperature of 220° C. The contact angle data for the material with and without SMM illustrate that the SMMs have altered the surface chemistry of the native polyethersulfone (see Tables 17, 18 and 19).

TABLE 17

Water/air Contact Angle Data for MDI-PCL(530)322L in Victrex 4800P

| MDI-PCL(530)322L concentration in Victrex 4800P, wt % | Advancing contact angle (degrees) | Receding contact angle (degrees) | Hysteresis (degrees) |
|---|---|---|---|
| 0 | 77 +/- 2 | 49 +/- 3 | 27 |
| 4 | 113 +/- 1 | 30 +/- 4 | 82 |

TABLE 18

Water/air Contact Angle Data for MDI-PPO(425)FSO1 in Victrex 4800P

| MDI-PPO(425)FSO1 concentration in Victrex 4800P, wt % | Advancing contact angle (degrees) | Receding contact angle (degrees) | Hysteresis (degrees) |
|---|---|---|---|
| 0 | 77 +/- 2 | 49 +/- 3 | 27 |
| 4 | 103 +/- 2 | 33 +/- 5 | 70 |

TABLE 19

Water/air Contact Angle Data for MDI-PPO(425)322L in Victrex 4800P

| MDI-PPO(425)322L concentration in Victrex 4800P, wt % | Advancing contact angle (degrees) | Receding contact angle (degrees) | Hysteresis (degrees) |
|---|---|---|---|
| 0 | 77 +/- 2 | 49 +/- 3 | 27 |
| 4 | 107 +/- 1 | 58 +/- 4 | 49 |

EXAMPLE 26

SMMs in admixture with polymers for blood contacting applications.

SMMs have been synthesized, and when added to polymers of medical significance, can be used to alter biological interactions at the surface of the materials. For instance, the interaction of enzymes with the surface of polyurethanes as illustrated in examples 1,6 and 8. A further requirement of blood contacting polymers is that they show minimal activation of blood components. The following example illustrates the platelet and white blood cell reactivity of 3 different SMMs (HDI-PPO212L, HDI-PPO322I, HDI-PTMO322I) with two polyurethanes, namely TDI/PCL/ED and MDI/PTMO/ED. The SMMs were mixed with 10% solutions of TDI/PCL/ED and 5% solutions MDI/PTMO/ED in dimethylacetamide. The amount of SMM relative base polymer was 5% by weight. The solutions were used to coat glass tubes which were then mounted to a rocking platform apparatus. Briefly, 550 mL of fresh heparinized whole blood was added to each tube and the ends of the tubes were connected to arms extending from a rocking platform. The whole blood was gently rocked within the tubes for one hour at 37° C. before flow cytometric analysis of the bulk whole blood was displaced from the tubes with buffer [Gemmell C., Ramirez, S. M., Yeo, E. L., Sefton, M. V., "Platelet activation in whole blood by artificial surfaces; identification of platelet-derived microparticles and activated platelet binding to leukocytes as material-induced activation events", J. Lab. Clin. Med. (1995) 125(2), 276–287.]. Blood was analyzed for platelet activation by measurement of P-selectin expression and formation of microparticles and determination of platelet count. The n-value for the experiment was 3 and Silastic and polyethylene surfaces were used as standards. Activation of white blood cells (monocytes and neutrophils) was determined by measuring up-regulation of CD11b. The data are presented in Table 20. Silastic elastomers are considered to be good standard reference materials in terms of expressing minimal blood cell activation. It can be observed that there are no statistical differences between Silastic and any of the modified materials with respect to platelet and white blood cell activation. This suggests that in addition to all the other attributes that the SMM materials have, they show minimal levels of blood cell activation, therefore indicating their potential application in medical devices. Relative to polyethylene the SMM polyurethanes induce less platelet loss.

TABLE 20

Platelet and White Blood Cell Activation Data for admixtures of SMMs and Polyurethanes.

| | Platelets | | | Neutrophils and Monocytes CDIIb |
|---|---|---|---|---|
| Test Groups | Platelet Count % Resting WB | % Microparticles | % P-selectin Positive | Expression (arbitrary fluorescence units) |
| Resting whole blood | 100 | 7 ± 3 | 2 ± 1 | 100 |
| Silastic | 89 ± 10 | 14 ± 2 | 2 ± 1 | 145 ± 39 |
| Polyethylene | 64 ± 8 | 17 ± 3 | 4 ± 4 | 132 ± 34 |
| 10% TDI/PCL/ED (Base) | 96 ± 6 | 8 ± 2 | 1 ± 1 | 152 ± 55 |
| Base + 5% PPO212L | 88 ± 15 | 14 ± 10 | 3 ± 3 | 136 ± 47 |
| Base + 5% PPO322I | 88 ± 10 | 10 ± 1 | 2 ± 1 | 156 ± 67 |
| Base + 5% PTMO322I | 84 ± 12 | 9 ± 1 | 3 ± 3 | 140 ± 69 |
| 10% MDI/ | 91 ± 16 | 9 ± 4 | 2 ± 3 | 151 ± 66 |

TABLE 20-continued

Platelet and White Blood Cell Activation Data for admixtures of SMMs and Polyurethanes.

| Test Groups | Platelets | | | Neutrophils and Monocytes CDIIb |
| --- | --- | --- | --- | --- |
| | Platelet Count % Resting WB | % Micro-particles | % P-selectin Positive | Expression (arbitrary fluorescence units) |
| PTMO/ED (Base) | | | | |
| Base + 5% PPO212L | 79 ± 24 | 13 ± 6 | 2 ± 2 | 143 ± 47 |
| Base + 5% PPO322I | 79 ± 11 | 17 ± 10 | 2 ± 1 | 139 ± 46 |
| Base + 5% PTMO322I | 88 ± 21 | 15 ± 11 | 3 ± 3 | 132 ± 36 |

Effective covalent chemistry to assemble the three components of SMMs.

While the examples hereinbefore reflect the specific use of diisocyanate chemistry to assemble the SMMs it will be understood by the person skilled in the art that other covalent link chemistries and specifically those generating similar polar functionality to urethanes, i.e. amides, urea, esters, carbonates, sulfonamides, may be used as substitute covalent links. The functional groups of interest that form, for example, urethane, amide, urea, ester, carbonate or sulfonamides can be devided into two reactive groups, viz: group A containing carboxylic acid, amine and hydroxyl groups, and group B containing carboxylic acids, isocyanates, acid halides, aldehydes and sulfonyl halides.

Although this disclosure has described and illustrated certain preferred embodiments of the invention, it is to be understood that the invention is not restricted to those particular embodiments. Rather, the invention includes all embodiments which are functional equivalents of the specific embodiments and features that have been described and illustrated herein.

I claim:

1. A surface modifying macromolecule having
   i) a non-chain extended central portion of a segmented block copolymer having a molecular weight of less than 2,000 and comprising a total of no more than ten units A and B, wherein A is a urethane containing group; and B is selected from the group consisting of a polyalkylene oxide, polycarbonate, polyester and lactone; and
   ii) α-ω terminal polyfluoro oligomeric groups.

2. A macromolecule as defined in claim 1 wherein said -ω terminal perfluoralkyl group is selected from the group consisting of radicals of the general formula: $CF_3(CF_2)_pCH_2CH_2$— wherein p is 5–9 and $CF_3(CF_2)_m(CH_2CH_2O)_n$— where n is 1–10 and m is 1–20.

3. A macromolecule as defined in claim 2 wherein said perfluoralkyl group is $C_8F_{17}CH_2CH_2$—.

4. A macromolecule as defined in claim 1 wherein said segmented block copolymer unit has a molecular weight selected from 200–1,200.

5. A surface modifying macromolecule having
   iii) a non-chain extended central portion of a segmented block copolymer having a molecular weight of less than 5,000 and comprising a total of no more than ten monomeric units A and B wherein A is a urethane containing group; and B is selected from the group consisting of a polyalkylene oxide, polycarbonate, polyester and lactone; and
   iv) α-ω terminal polyfluoro oligomeric groups, selected from $CF_3(CF_2)_pCH_2CH_2$— wherein p is 5–9 and $CF_3(CF_2)_m(CH_2CH_2O)_n$— where n is 1–10 and m is 1–20.

6. A macromolecule according to claim 5 wherein said segmented block copolymer has a molecular weight of from 200–1,200 and the perfluoroalkyl group is $C_8F_{17}CH_2CH_2$—.

7. A macromolecule as defined in claim 1 or 5 wherein said segmented block copolymer is formed by the reaction of a diisocyanate with a compound selected from the group consisting of a polyalkylene oxide polyol, polycarbonate polyol, polyester polyol and a lactone polyol.

8. A macromolecule as defined in claim 7 wherein said polyalkylene oxide polyol is selected from a group consisting of polyethylene oxide, polypropylene oxide and polytetramethylene oxide.

9. A macromolecule as defined in claim 7 wherein said lactone polyol is capolactone diol.

10. A macromolecule as defined in claim 7 wherein said diisocyanate is selected from the group consisting of 2,4 toluene diisocyanate, 2,6 toluene diisocyanate, methylene bis(p-phenyl) diisocyanate, 1,5 naphtanene diisocyanate, 3,3' bitoluene diisocyanate, methylene bis (p-cyclohexyl isocyanate), 1,6 hexane diisocyanate, 1,12 dodecane diisocyanate, isophorone diisocyanate, and cyclohexyl diisocyanate.

11. A method of producing the surface modifying macromolecule according to claim 1 or claim 5 comprising
    (a) polymerizing a multi-functional precursor for unit A with a compound selected from the group consisting of polyalkylene oxide polyol, polycarbonate polyol, polyester polyol and lactone polyol to form a segmented copolymer precursor; and
    (b) reacting said copolymer precursor with a perfluoroalkyl alcohol to produce said macromolecule.

12. A method as defined in claim 11 comprising the steps of
    (a) polymerizing a diisocyanate with a compound selected from the group consisting of a polyalkylene oxide, polyester diol and a lactone diol to form a polyurethane precursor; and
    (b) reacting said polyurethane precursor with a perfluoroalkyl alcohol to form a macromolecule having a central portion segmented block oligomeric copolymer having a polyurethane hard segment and α-ω perfluoroalkyl terminal groups.

13. A shaped article comprising the surface modifying macromolecule of claim 1 or claim 5 in admixture with a base polymer.

14. An article as defined in claim 13 wherein said base polymer is selected from the group consisting of polyurethanes, polysulfones, polycarbonates, polyesters, polyethylene, polyproprylene, polystyrene, poly (acrylonitrile-butadienestyrene), polybutadiene, polyisoprene, styrenebutadiene-styrene block copolymers, styrene-iso-prenestyrene block copolymers, poly-r-methylpentene, polyisobutylene, polymethyl-methacrylate, polyvinylacetate-polyacrylonitrile, polyvinyl chloride, polyethylene terephthalate, cellulose and its esters and derivatives, polyamides, polyester-polyethers,styrene-isoprenes, styrene butadienes, thermoplastic polyolefins, styrene-saturated olefins, polyester-polyester, ethylene-vinyl acetate ethylene-ethyl acrylate, ionomers, and thermoplastic polydienes.

15. An article as defined in claim 13 wherein said base polymer is a segmented polyurethane.

16. An article as defined in claim 13 wherein said segmented block copolymer is formed by the reaction of a diisocyanate with a polyalkylene oxide polyol.

17. An article as defined in claim 13 wherein said -ω terminal perfluoroalkyl group is selected from the group consisting of radicals of the general formula:

$CF_3(CF_2)_p CH_2CH_2-$ where p is 5–9; and $CF_3(CF_2)_m(CH_2CH_2O)_n-$ where n is 1–10 and m is 1–20.

18. An article as defined in claim 13 being an implantable medical device having a hemocompatible surface comprising said base polymer in admixture with said macromolecule.

* * * * *